United States Patent
Hasegawa et al.

(10) Patent No.: US 6,329,548 B1
(45) Date of Patent: Dec. 11, 2001

(54) AQUEOUS STABLE LYSINE SOLUTION

(75) Inventors: Kazuhiro Hasegawa; Toshiya Tanabe; Keita Minami, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/518,094

(22) Filed: Mar. 3, 2000

(30) Foreign Application Priority Data

Mar. 11, 1999 (JP) .................................. 11-064625

(51) Int. Cl.⁷ .......................... C07C 229/00; B41L 1/26; B41L 1/10
(52) U.S. Cl. .............................. 562/562; 562/561; 426/2; 426/69
(58) Field of Search ..................... 562/562, 561; 426/2, 69

(56) References Cited

U.S. PATENT DOCUMENTS 4,919,945 * 4/1990 Spindler et al. .

FOREIGN PATENT DOCUMENTS

| | | |
|---|---|---|
| 0 111 628 | 6/1984 | (EP) . |
| 0 534 865 | 3/1993 | (EP) . |
| 07-309750 | 11/1995 | (JP) . |
| 171727 | 5/1965 | (RU) . |
| 835 404 | 5/1981 | (RU) . |
| 171 727 | 8/1993 | (RU) . |
| WO 96/40618 | 12/1996 | (WO) . |
| WO 99/27799 | 6/1999 | (WO) . |

* cited by examiner

*Primary Examiner*—Paul J. Killos
*Assistant Examiner*—Mahreen Chaudhry
(74) *Attorney, Agent, or Firm*—Oblon, Spivak, McClelland, Maier & Neustadt, P.C.

(57) ABSTRACT

Herein is disclosed an aqueous stable lysine solution containing an acid radical in such amount that the solubility of lysine therein has been increased than in the corresponding aqueous lysine base solution, whereby during storage of lysine in the form of a free-lysine solution (liquid composition), the precipitation of lysine base crystals due to the drop in temperature is prevented thereby improving the handling thereof during transportation (transfer) etc.

26 Claims, 1 Drawing Sheet

AQUEOUS STABLE LYSINE SOLUTION

BACKGROUND OF THE INVENTION

1. Technical Field to Which the Invention Belongs

The present invention relates to the stabilization of a lysine solution, and in particular to the stabilization of a lysine solution by incorporating a predetermined amount of an acid radical therein.

Incidentally, the acid radical is the residue of an acid molecule from which one or more hydrogen atoms capable of being replaced by metal(s) have been removed, and it constitutes the negative moiety of a salt. The acid radical often refers to an atomic group such as the acid radical ($SO_4$) of sulfuric acid, but a single atom such as Cl in hydrogen chloride is also referred to as an acid radical, this nomenclature being followed in this specification.

Furthermore, the solubility of lysine refers to the equilibrium maximum amount of lysine soluble in unit water amount of a lysine solution.

Still furthermore, the product of the molar number of an acid radical multiplied by its valence refers, e.g., to the molar number of the acid radical when the acid radical consists of a monovalent acid radical only, or to the product of the molar number of the acid radical multiplied by 2 as its valence when the acid radical consists of a divalent acid radical only, or to the sum of the molar number of a monovalent acid radical and the product of the molar number of a divalent acid radical multiplied by 2 as its valence when the acid radical consists of both monovalent and divalent acid radicals.

2. Prior Art

As is well-known, lysine is used as one of the essential amino acids in a large amount as a feed additive for producing a feed for domestic animals such as cattle, pigs and chickens as well as an industrially produced mixed feed. In so doing, however, lysine is not used as crystals in the free and pure form but used usually in the form of monohydrochloride, because lysine is readily soluble in water, is hardly crystallized in the free form, exhibits strong moisture absorption (i.e., is strongly hygroscopic), absorbs carbon dioxide from the air, possesses a significantly unpleasant odor and is liable to degradation. In the present specification, lysine means lysine in the L-form (i.e. L-lysine) except quotations from the prior art literature and is referred to as "lysine base" when it is intended to emphasize that lysine is not in a salt form but in the free form (free lysine)

The monohydrochloride is a compound which is stable, not liable to degradation and readily crystallized, and does not possesses properties such as moisture absorbing and unpleasantly smelling. However, its production involves the problems of additional raw material costs and process costs. Further, the use of lysine monohydrochloride for enriching lysine in feeds and industrially produced mixed feeds increases not only the content of lysine but also the content of chlorides in the mixed feeds, but this is generally undesired. Further, the ratio of lysine to chlorides is also important. This is because, in feeding experiments with crystalline amino acid feeds, it is often observed that the positive effects of the amino acid added are completely lost, when the amino acid is used as the hydrochloride, whereby the chloride excess, in turn, occurs. For these reasons, lysine in the chloride-free form has been strongly desired for the purpose of nutritional enrichment for feeds and industrially produced mixed feeds.

Under such technical background, the JP-B 3-5783 patent document discloses an invention titled "A process for producing a feed and an industrially produced mixed feed enriched with lysine wherein an aqueous L-lysine solution containing 30 to 80 weight % L-lysine is used".

With respect to the findings on which this prior art invention is based, said document states, "It has been found that when L-lysine is used in the form of an aqueous solution for enrichment, L-lysine, which is unstable in the free form, can be used for enrichment of feeds and mixed feeds. It has been unexpected that the aqueous solution is stable even at high temperatures in storage for a long time. A comparative experiment has showed that an aqueous 70% L-lysine solution is not colored at all after storage at 50° C. for 6 weeks. An experiment on by-products which may be formed depending on the condition has also indicated minus. As compared with the product in solution, crystalline L-lysine is evidently colored during this storage. Formation of by-products has been confirmed in an analytical experiment. Accordingly, the found behavior described above has been absolutely unexpected, because general experience teaches that products liable to degradation are more easily degraded in a dissolved form than in a crystalline form". The patent document makes comments on the advantages of the invention, "An aqueous solution of lysine can be produced easily as compared with crystalline L-lysine monohydrochloride, and the aqueous solution has the advantage that the content of chlorides in mixed feeds is not increased and the solution can be accurately metered even in a small amount. When a mixed feed is to be enriched with L-lysine, the L-lysine as a liquid composition does not usually require inevitable production of a pre-mixture having L-lysine at a correspondingly high concentration. The aqueous solution of lysine can, directly at a desired concentration, be mixed uniformly with other ingredients previously present at desired concentrations in a mixed feed, for example by sprinkling the lysine solution in a mixing cooker." Concerning the unexpectedness of the invention, the document additionally states, "Although L-lysine is referred to as one kind of amino acid which is destroyed first of all by heat treatment not only in materials but also in feeds and mixed feeds—this free L-lysine is added in the form of an aqueous L-lysine solution, and is unexpectedly stable even in feeds and mixed feeds. Degradation and/or reaction does not occur due to other feed ingredients. In a feeding experiment, an aqueous L-lysine solution and L-lysine monohydrochloride exhibit the same action insofar as these are used in the same molar amount".

The patent document describes, concerning the concentration of the aqueous lysine solution of the invention disclosed therein, "To achieve the desired improvement as to weight increase and utilization of feed, various amounts of L-lysine should be added to each mixed feed in order to compensate for the content of natural L-lysine in feed protein. To use an aqueous L-lysine solution according to the present invention, the amount thereof is generally 0.01 to 5%, relative to the weight of the finished mixed feed, depending on the concentration of the L-lysine in the solution. In this case, a solution with a L-lysine content of 30 to 80% by weight, advantageously 50 to 70% by weight, is particularly preferable.", and in respect of the process for producing the same, the document states, "Such a solution is obtained by dissolving L-lysine in a corresponding amount of water. In commercially producing L-lysine, it is naturally easy and suitable to produce an aqueous solution containing L-lysine at a desired concentration during the commercial production of L-lysine. This evidently facilitates production and does not so cost as in production of particularly L-lysine monohydrochloride."

For nutritionally enriching feeds or industrially produced mixed feeds with lysine, lysine in the form of a liquid composition possesses such various advantages as described in JP-B 3-5783 supra, but the liquid composition of lysine described in the patent document involves the problem that the lysine is easily precipitated as free form lysine crystals as the temperature of the atmosphere drops during storage. Precipitation of such crystals will, in turn, cause clogging of pipes for transferring the liquid composition of lysine in factories or during shipping and unloading or make it difficult to transfer the liquid composition of lysine at a predetermined concentration, thus worsening the handling of the liquid composition of lysine.

To sum up, when lysine is used in the form of a liquid composition, a lysine base solution has been used in many cases because of higher solubility than in a lysine salt solution such as lysine hydrochloride solution, lysine sulfate solution etc. However, from the conventional lysine base solution with a concentration of not less than 50% by weight, as described in JP-B 3-5783 supra, lysine base is crystalized when the temperature drops during storage, to cause, e.g., clogging of piping, thus worsening the handling in some cases.

SUMMARY OF THE INVENTION
Problems to Be Solved by the Invention

Under the technical background described above, an object of the present invention is to provide a method wherein during storage of lysine in the form of a freelysine solution (liquid composition), the precipitation of lysine base crystals due to the drop in temperature is prevented thereby improving the handling thereof during transportation (transfer) etc. This object can be achieved after all by raising the solubility of lysine in a lysine base solution, and thus the object of the present invention is, in other words, to provide a method of improving the solubility of lysine in an aqueous lysine solution thus preventing precipitation of lysine crystals during storage and transportation to improve its handling.

The raised solubility of lysine in a lysine solution leads to improvement of the handling of the lysine solution (liquid composition) and the high-conc. lysine solution (high-conc. liquid composition) thus provided, in turn, brings about the advantages that it contributes to a reduction in the cost for transportation of lysine solutions or that operational costs can be reduced in spray-granulating by feeding a high-conc. solution.

Means to Solve the Problems

As a result of their eager study, the present inventors have found that the acid radical of, e.g., hydrochloric acid (or hydrochloride) or sulfuric acid (or sulfate) is added at a predetermined ratio to the lysine, to an aqueous lysine base solution, whereby the solubility of lysine can be raised than in the original aqueous lysine base solution (as a matter of course, the comparison having been conducted at a certain temperature), and on the basis of these findings, the present invention has been completed.

Accordingly, the present invention relates to an aqueous stable lysine solution containing an acid radical in such amount that the solubility of lysine therein has been increased than in the corresponding an aqueous lysine base solution, said corresponding aqueous lysine base solution meaning an aqueous lysine base solution having the same composition as said aqueous stable lysine solution of the present intention except with no acid radical contained therein.

DETAILED DESCRIPTION OF THE INVENTION

Figure 1:
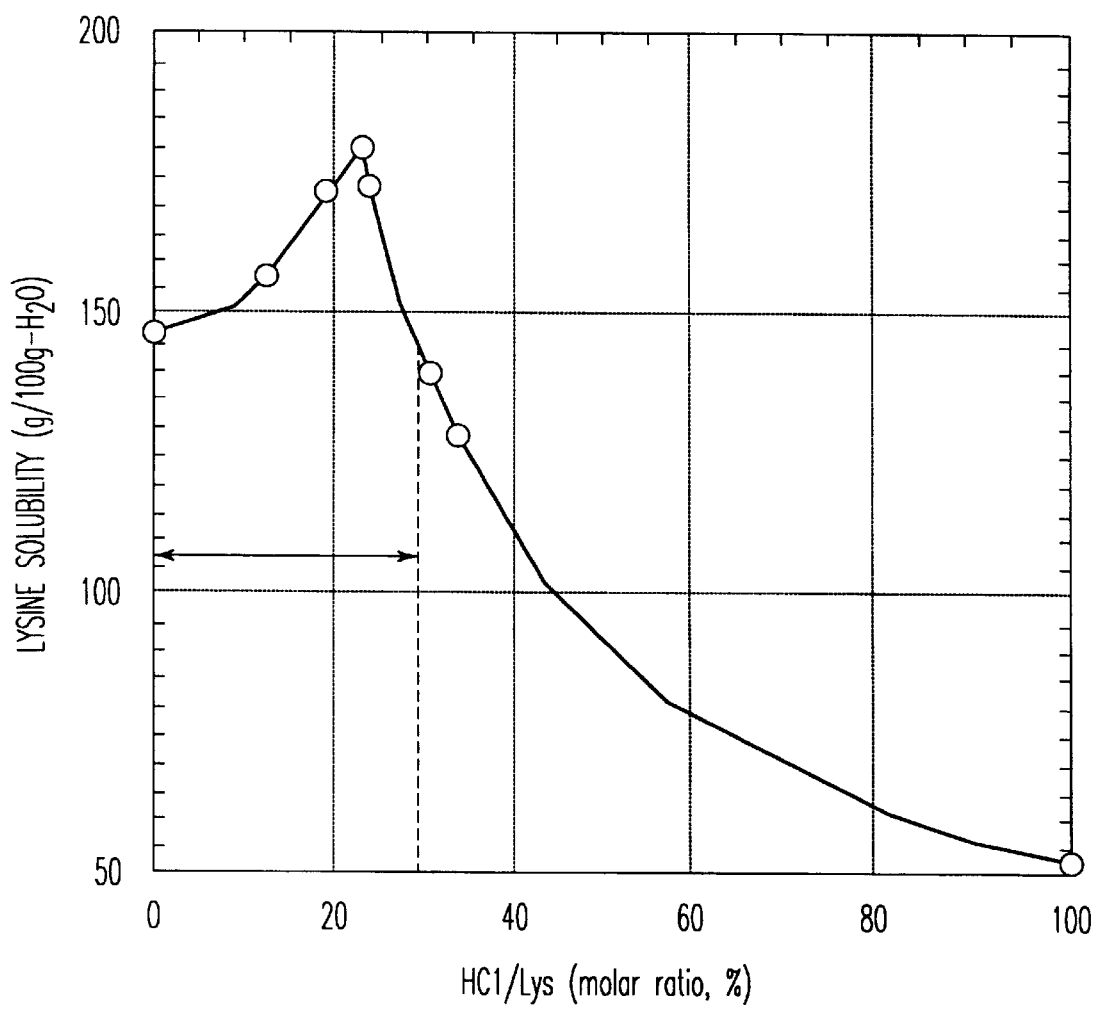
FIG. 1 shows the solubility curve at 20° C. of lysine depending on the amount of hydrochloric acid relative to the lysine (Example 1).

Hereinafter, the present invention will be described in more detail.

The aqueous stable lysine solution of the present invention (liquid lysine composition) is an aqueous lysine solution containing an acid radical at a predetermined ratio of the acid radical to the lysine. Incidentally, such a liquid lysine composition containing an acid radical at a predetermined ratio of the acid radical to the lysine is a novel material (novel composition). This is because the Japanese patent document supra refers to an aqueous lysine base solution only, with respect to the process for producing the liquid lysine composition, as in: "Such a solution is obtained by dissolving L-lysine in a corresponding amount of water" as quoted above, and an aqueous lysine solution containing an acid radical at the ratio specified according to the present invention has not been known in any other prior art literatures.

Further, it is not easy from the prior art to find an aqueous lysine base solution containing an acid radical at such ratio that the solubility of lysine is higher at a certain temperature than in its corresponding aqueous lysine base solution containing no such acid radical at the same temperature. As has been described above, lysine base is readily soluble in water, while lysine monohydrochloride is readily crystallized. It is reasonable therefrom to estimate that when hydrochloric acid is gradually added to an aqueous lysine base solution, the solubility of lysine is gradually decreased as the concentration of hydrochloric acid is increased, thus bringing about crystallization of lysine monohydrochloride, and it is difficult to estimate that the solubility of lysine base is increased transiently during the course in which the ratio of hydrochloric acid is raised until lysine monohydrochloride is crystallized, as found by the present inventors.

The aqueous stable lysine solution of the present invention can be prepared very easily by those who are skilled in the art. This is because lysine base crystals or lysine salt crystals are dissolved at a certain temperature in a lysine base solution or in its corresponding lysine base solution containing an acid radical, and then the amount of the acid radical relative to the lysine in the solutions and the solubility of lysine therein are measured, thereby plotting the solubility curve of lysine depending on the amount of the acid radical relative to the lysine so that the desired amount (range) of the acid radical relative to the lysine can be easily determined.

Of course, the aqueous stable lysine solution of the present invention can be easily prepared by adding an acid radical to a lysine base solution at a suitable ratio of the acid radical to the lysine, and there are no limits thereto. Alternatively, the aqueous stable solution can be prepared by any of the following methods:

(1) A lysine-containing solution such as a lysine salt solution or a mother liquor remaining after the lysine has been precipitated as a salt thereof from a lysine fermentation broth or a reaction mixture resulting from lysine fermentation, lysine synthesis or protein hydrolysis, is passed through a cation-exchange resin, whereby the lysine is adsorbed onto it. Thereafter, the adsorbed lysine is eluted with, e.g., ammonia water or the like, and the eluate is concentrated while the ammonia is removed, to prepare a lysine base solution. A suitable amount of an acid radical is added to this lysine base solution, whereby the desired aqueous stable lysine solution can be prepared.

Here, the phrase "an acid radical is added" concretely means addition of a free acid such as hydrochloric acid or sulfuric acid, or its salt (sodium chloride, ammonium sulfate etc.) . This is because the free acid and its salt both contain an acid radical.

(2) Calcium hydroxide, barium hydroxide etc. are added to such lysine-containing solution described above, whereby an excess sulfate radical contained therein is removed by precipitating it as sparingly soluble salts such as barium sulfate until the acid radical has been reduced to a predetermined level. Thus, the aqueous stable lysine base solution can be obtained.

(3) The lysine-containing solution described above is passed through an OH-form anion-exchange resin so that the acid radical is removed by adsorbing it onto the resin, whereby the aqueous stable lysine solution with a predetermined amount of the acid radical can be obtained. In this case, the acid radical may be removed until it is reduced to a predetermined level, and it is naturally not necessary to remove all the acid radical moiety.

(4) A lysine base solution obtained from the above lysine-containing solution by the method described in (1) above is mixed with a lysine salt solution such as a lysine hydrochloride solution, or with an acid radical-containing solution resulting from fermentation or synthesis, or with a mother liquor remaining after lysine hydrochloride crystals has been crystallized, whereby the aqueous stable lysine solution with a predetermined amount of the acid radical can be obtained.

The lysine stable solution of the present invention may contain cations, proteins, organic acids etc. derived from a lysine fermentation broth or a lysine synthetic mixture unless the effects of the present invention are deteriorated.

The thus obtained lysine base solution containing an acid radical from an acid such as hydrochloric acid, sulfuric acid, or the like is a novel composition as described above and possesses the effects of preventing the precipitation of lysine base crystals at lower temperatures during storage while providing a higher conc. solution.

Hereinafter, the foregoing will be described in more detail.

FIG. 1 shows the solubility curve of lysine at, e.g., 20° C. depending on the amount of the hydrochloric acid relative to the lysine, as measured by the present inventors (Example 1 infra). The solubility (g) of lysine per 100 g water is shown on the ordinate, while the molar ratio (%), relative to the lysine, of the hydrochloric acid in the solution is shown on the abscissa.

According to the findings of the present inventors, also at other temperatures such as 30° C. or −20° C. and also with respect to other acids such as sulfuric acid etc., the solubility of lysine is increased in all the temperature range until a certain point in the molar ratio, while the molar ratio of an acid radical to the lysine is increased from 0.

As can be seen from FIG. 1, an aqueous lysine base solution containing lysine in an amount of the solubility at 20° C. but no hydrochloric acid (which is an aqueous saturated lysine solution) becomes supersaturated when the temperature is lowered to less than 20° C., to precipitate lysine bas e crystals. On the contrary, however, if hydrochloric acid is contained in a predetermined range, even an aqueous lysine solution containing the same amount of lysine per unit water amount of the solution at the same temperature hardly becomes supersaturated even if the temperature is lowered to some degree, thus preventing precipitation of lysine crystals.

The aqueous stable lysine solution according to the present invention means an aqueous lysine solution from which, owing to incorporation of an acid radical at a predetermined ratio of the acid radical to the lysine, lysine crystals are hardly precipitated upon a drop in temperature as compared with a lysine base solution containing no acid radical (in order words, the solution is stabilized with respect to precipitation of lysine crystals upon a drop in temperature).

As can be seen also from FIG. 1, the lysine solution containing hydrochloric acid can contain, e.g., at 20° C. lysine at higher concentrations per unit amount of water (e.g., weight) than in the corresponding lysine base solution containing no hydrochloric acid.

In the aqueous stable lysine solution containing an acid radical, from which lysine base crystals are hardly precipitated upon temperature change (−30 to 80° C.) in a practical atmosphere, the content of the acid radical is preferably 35% or less, more preferably in the range of 1 to 27%, and still more preferably in the range of 5 to 25%, in terms of the ratio of the product of the molar number of the acid radical multiplied by the valence of the acid radical to the molar number of lysine.

The acid radical is preferably the chloride radical, the sulfate radical or a mixture thereof. As described above, the chloride radical includes the one derived from hydrochloric acid or salts such as sodium chloride, potassium chloride and ammonium chloride, and the sulfate radical includes the one derived from salts such as sodium sulfate, sodium hydrogen sulfate, potassium sulfate and ammonium sulfate. If the acid radical is the chloride radical, the content thereof is preferably 35% or less, more preferably in the range of 1 to 27%, and still more preferably in the range of 5 to 25%, in terms of the ratio of the molar number of the chloride radical to the molar number of the lysine. If the acid radical is the sulfate radical, the content thereof is preferably 17% or less, more preferably in the range of 2 to 13%, and still more preferably in the range of 6 to 13%, in terms of the ratio of the molar number of the sulfate radical to the molar number of the lysine. If the acid radical is a mixture of the chloride radical and the sulfate radical, the content of the mixture is preferably 35% or less, more preferably in the range of 1 to 27%, and still more preferably in the range of 5 to 25%, in terms of the ratio of the sum of the molar number of the chloride radical and the product of the molar number of the sulfate radical multiplied by 2 as its valence to the molar number of the lysine.

There are no particular difficulties in a process per se for producing a lysine-enriched feed or an industrially produced mixed feed by the use of the aqueous stable lysine solution of the present invention, and conventional known techniques using lysine in the form of a liquid composition, for example, the techniques described in JP-B 3-5783 supra can be used. That is, the desired feed can be produced in the same manner as described in the patent document supra except that the aqueous stable lysine solution of the present invention is used in place of the "aqueous L-lysine solution" referred to therein.

EXAMPLES

The present invention will be described in more detail by reference to the Examples.

Example 1

(1) 1,015 g of medical grade lysine hydrochloride anhydride crystals were dissolved in 5,000 g of deionized water and the mixture was adjusted to pH 3.0 with reagent grade 35% hydrochloric acid. The solution was passed at a flow rate of 19 L/hr through a column packed with 19 L of $NH^+$-form cation-exchange resin ("Diaion SK-1B", ex Mitsubishi Chemical Industries Ltd.), whereby the lysine was adsorbed onto the cation-exchange resin. After adsorption, the column was washed by passing 38 L of deionized water therethrough at the same flow rate of 19 L/hr, and after 38 L of 2 N ammonia water was passed through the column at the same flow rate of 19 L/hr, 38 L of deionized water was passed therethrough at the same rate of 19 L/hr, whereby the lysine was eluted. 76 L of this eluted lysine solution was concentrated under reduced pressure (50 mmHg) until the lysine concentration reached 70%, whereby a lysine base solution was obtained. These procedures were repeated 5 times, whereby 4,600 g of aqueous 70% lysine solution was obtained.

(2) A 1,800 g portion of the lysine base solution with a lysine concentration of 70% obtained under (1) above was stirred under cooling at a rate of −10° C./hr from 50° C. to 10° C. so that lysine base crystals were precipitated. The crystals were separated and air-dried, whereby 500 g of lysine base crystals were obtained.

(3) 390 g of medical grade lysine hydrochloride anhydride crystals were introduced into 300 g of deionized water and dissolved by raising the temperature to 60° C. in a water bath. The solution was stirred under cooling to 15° C. at a rate of −10°C./hr, whereby lysine hydrochloride.$2H_2O$ crystals were precipitated. The crystals were separated and air-dried to give 280 g of lysine hydrochloride.$2H_2O$ crystals.

70% lysine base solution obtained under (1) above, 35% hydrochloric acid and deionized water were used in the amounts shown in Table 1 below, respectively, to prepare 7 kinds of solutions. In these solutions, the lysine base crystals obtained under (2) above and the lysine hydrochloride.$2H_2O$ crystals obtained under (3) above were suspended respectively in the amounts shown in the same table, and then stirred for 1 week during which the temperature was kept at 20° C.

The crystals were removed from these suspensions, and the concentration of the chloride ions in each of the remaining solutions was analyzed by an ion chromatographic analyzer "Yokokawa IC7000 model", and the concentration of lysine therein was analyzed by an amino acid analyzer "Hitachi L-8500 model". The results are also shown in FIG. 1 below.

TABLE 1

| | Experimental Conditions | | | | |
|---|---|---|---|---|---|
| Operation No. | 70% lysine solution (g) | 35% hydrochloric acid (g) | deionized water (g) | lysine base crystals (g) | lysine hydrochloride crystals (g) |
| 1 | 350 | 0 | 58 | 40 | |
| 2 | 377 | 22 | 46 | 106 | |
| 3 | 378 | 38 | 32 | 155 | |
| 4 | 365 | 52 | 42 | 147 | 4.2 |
| 5 | 326 | 28 | 41 | 49 | 54 |
| 6 | 401 | 52 | 42 | 1.6 | 19 |
| 7 | 397 | 68 | 38 | 1.8 | 22 |

As can be seen from FIG. 1, the solubility of lysine is increased when the chloride ions (the chloride radical) are contained at a molar ratio of 27% or less to the lysine, as compared with the case where the chloride ions are not contained.

Example 2

Lysine base crystals obtained in the same manner as in Example 1(2), lysine hydrochloride.$2H_2O$ crystals obtained in the same manner as in Example 1(3) and deionized water were used respectively in the amounts show in Table 2 below to prepare 5 kinds of suspensions, and each suspension was stirred for 1 week during which the temperature was kept at 30° C. or −20° C.

The crystals were removed from these suspensions, and the concentration of the chloride ions in each of the resulting solutions (supernatants) was analyzed by the ion chromatographic analyzer "Yokokawa IC7000 model", and the concentration of the lysine therein was analyzed by the amino acid analyzer "Hitachi L-8500 model". The results are also shown in the same table.

TABLE 2

| | Experimental Conditions | | | | Results of Analysis of Supernatant Components | | |
|---|---|---|---|---|---|---|---|
| Operation No. | deionized water (g) | lysine hydrochloride crystals (g) | lysine base crystals (g) | temperature (° C.) | Chloride ion concentration (wt %) | solubility of lysine (g/100 g-$H_2O$) | HCl/Lys (molar ratio) |
| 1 | 40 | 0 | 95 | 30 | 0 | 160 | 0% |
| 2 | 37 | 30 | 80 | 30 | 3.4 | 175 | 22.8% |
| 3 | 36 | 35 | 80 | 30 | 3.9 | 179 | 26.0% |
| 4 | 37 | 45 | 58 | 30 | 5.0 | 160 | 35.0% |
| 5 | 44 | 0 | 60 | −20 | 0 | 102 | 0% |
| 6 | 43 | 8 | 55 | −20 | 1.4 | 106 | 11.5% |

As can be seen from the table, the solubility of lysine is increased too at varied temperatures by incorporating chloride ions (i.e., chloride radical).

Example 3

300 g of 60% lysine base solution obtained in the same manner as in Example 1(1) was placed in a water bath and 63.5 g of reagent grade 95% sulfuric acid was gradually added thereto. After addition of sulfuric acid was finished, the mixture was kept at a temperature of 50° C. and then stirred under cooling from that temperature to 10° C. at a rate of −10° C./hr, to precipitate lysine sulfate crystals. The crystals were separated and air-dried to give 90 g of lysine sulfate crystals. The lysine sulfate crystals, lysine base crystals obtained in the same manner as in Example 1(2) and deionized water were used respectively in the amounts shown in Table 3 below to prepare suspensions, and each suspension was stirred for 1 week during which the temperature was kept at 20° C. The crystals were removed from these suspensions, and the concentration of the sulfate ions in each of the resulting solutions (supernatants) was analyzed by the ion chromatographic analyzer "Yokokawa IC7000 model", and the concentration of the lysine therein was analyzed by the amino acid analyzer "Hitachi L-8500 model". The results are also shown in the same table.

TABLE 3

| | Experimental Conditions | | | Results of Analysis of Supernatant Components | |
|---|---|---|---|---|---|
| Operation No | deionized water (g) | lysine sulfate crystals (g) | lysine base crystals (g) | sulfate ion concentration (wt %) | solubility of lysine (g/100g-$H_2O$) |
| 1 | 41 | 0 | 90 | 0 | 147 |
| 2 | 41 | 10 | 85 | 1.9 | 158 |
| 3 | 42 | 20 | 75 | 28 | 157 |

From the table, the effect of increasing the solubility of lysine by incorporating sulfate ions ($SO_4^{2-}$, sulfate radical) is recognized similarly to the case where chloride ions ($Cl^-$, chloride radical) are incorporated.

Example 4

A lysine base solution with a lysine concentration adjusted to 62% was prepared by adding 26.8 g of 35% hydrochloric acid to 241 g lysine base solution with a lysine concentration of 74.3% obtained in the similar manner as in Example 1(1) and then adding 22 g of deionized water thereto, and another lysine base solution with a lysine concentration adjusted to 62% was prepared by adding 48 g of deionized water to 239 g lysine base solution with a lysine concentration of 74.3%. The resulting solutions, that is, the lysine base solution containing hydrochloric acid and the lysine base solution containing no hydrochloric acid were stirred, respectively, in sealed vessels in a thermostatic bath at 20° C.

After 8 days, comparison of both solutions revealed that lysine base crystals had been precipitated in the system where hydrochloric acid was not added, whereas precipitation of crystals was not observed in the system where hydrochloric acid was added. Accordingly, the stability of the lysine base solution with respect to precipitation of crystals can be improved by incorporating hydrochloric acid (chloride ions).

Example 5

A lysine base solution with a lysine concentration of 75.6% obtained in the similar manner as in Example 1(1), aqueous 25% sodium chloride solution, aqueous 25% ammonium chloride solution and deionized water were used respectively in the amounts shown in Table 4 below, to prepare 2 kinds of solutions. Lysine base crystals obtained in the same manner as in Example 1(2) were suspended in these solutions in the amounts shown in the same table, and stirred for 1 week during which the temperature was kept at 20° C.

The crystals were removed from these suspensions, and the concentration of the chloride ions in each of the resulting solutions (supernatants) was analyzed by the ion chromatographic analyzer "Yokokawa IC7000 model", and the concentration of the lysine therein was analyzed by the amino acid analyzer "Hitachi L-8500 model". The results are also shown in the same table.

TABLE 4

| | Experimental Conditions | | | | | Result of Analysis of Supernatant Components | |
|---|---|---|---|---|---|---|---|
| Operation No. | 75.6% lysine solution (g) | 25% NaCl solution (g) | 25% $NH_4Cl$ solution (g) | deionized water (g) | lysine base crystals (g) | Chloride ion concentration (wt %) | Solubility of lysine (g/100 g-$H_2O$) |
| 1 | 151 | 36 | | 10 | 16 | 3.1 | 164 |
| 2 | 122 | | 27 | | 11 | 3.3 | 178 |

Effects of the Invention

According to the present invention, a free acid such as hydrochloric acid or sulfuric acid, or a lysine salt such as lysine hydrochloride or lysine sulfate is added to a lysine base solution at a predetermined ratio of the acid radical to the lysine in the solution, whereby the concentration of lysine can be made higher than in a solution of lysine base alone. That is, addition of an acid radical in these forms can make the lysine base solution stable at higher concentration, whereby even the lysine base solution can be stored without undergoing the precipitation of lysine base crystals due to, e.g., a drop in temperature, the cost for transportation of lysine solutions can be reduced, and in the case where the lysine solution is subjected to spray-granulation, the high-conc. solution can be sprayed.

Briefly, the solubility of lysine in water can be improved (i.e., increased) according to the present invention thereby preventing the precipitation of crystals upon a drop in temperature, and the stable lysine solution can be easily prepared at a higher concentration, thus improving the handling of the lysine solution during transportation etc.

What is claimed as new and desired to be secured by Letters Patent is:

1. An aqueous stable lysine solution comprising lysine and an acid anion in such amount that the solubility of lysine therein has been increased as compared to a corresponding aqueous lysine base solution, wherein the content of the acid anion is 35% or less in terms of the ratio of the product of the molar number of the acid anion multiplied by its valence to the molar number of the lysine.

2. The aqueous stable lysine solution as set forth in claim 1, wherein said acid anion is the chloride anion ($Cl^-$) and/or the sulfate anion ($SO_4^{2-}$).

3. The aqueous stable lysine solution as set forth in claim 1, wherein said acid anion is the chloride anion ($Cl^-$) and is contained within the range of 35% or less in terms of the molar ratio thereof to the lysine.

4. The aqueous stable lysine solution as set forth in claim 1, wherein said acid anion is the sulfate anion ($SO_4^{2-}$) and is contained within the range of 17% or less in terms of the molar ratio thereof to the lysine.

5. The aqueous stable lysine solution as set forth in claim 3, wherein chloride is contained within the range of 1–27% in terms of the molar ratio thereof to the lysine.

6. The aqueous stable lysine solution as set forth in claim 3, wherein chloride is contained within the range of 5–25% in terms of the molar ratio thereof to the lysine.

7. The aqueous stable lysine solution as set forth in claim 4, wherein said sulfate anion is contained within the range of 2–13% in terms of the molar ratio thereof to the lysine.

8. The aqueous stable lysine solution as set forth in claim 4, wherein said sulfate anion is contained within the range of 6–13% in terms of the molar ratio thereof to the lysine.

9. The aqueous stable lysine solution as claimed in claim 1, wherein said solution is an aqueous 70% lysine solution.

10. The aqueous stable lysine solution as claimed in claim 2, wherein said solution is an aqueous 70% lysine solution.

11. The aqueous stable lysine solution as claimed in claim 3, wherein said solution is an aqueous 70% lysine solution.

12. The aqueous stable lysine solution as claimed in claim 4, wherein said solution is an aqueous 70% lysine solution.

13. The aqueous stable lysine solution as claimed in claim 5, wherein said solution is an aqueous 70% lysine solution.

14. The aqueous stable lysine solution as claimed in claim 6, wherein said solution is an aqueous 70% lysine solution.

15. The aqueous stable lysine solution as claimed in claim 7, wherein said solution is an aqueous 70% lysine solution.

16. An aqueous stable lysine solution as claimed in claim 1, wherein said solution is an aqueous 60% lysine solution.

17. An aqueous stable lysine solution as claimed in claim 2, wherein said solution is an aqueous 60% lysine solution.

18. An aqueous stable lysine solution as claimed in claim 3, wherein said solution is an aqueous 60% lysine solution.

19. An aqueous stable lysine solution as claimed in claim 4, wherein said solution is an aqueous 60% lysine solution.

20. An aqueous stable lysine solution as claimed in claim 5, wherein said solution is an aqueous 60% lysine solution.

21. An aqueous stable lysine solution as claimed in claim 6, wherein said solution is an aqueous 60% lysine solution.

22. An aqueous stable lysine solution as claimed in claim 7, wherein said solution is an aqueous 60% lysine solution.

23. An aqueous stable lysine solution as claimed in claim 8, wherein said solution is an aqueous 60% lysine solution.

24. The aqueous stable lysine solution as claimed in claim 8, wherein said solution is an aqueous 70% lysine solution.

25. A method for enriching a feed, comprising mixing a feed base with the solution of claim 1.

26. A feed composition comprising a feed base and the solution of claim 1.

* * * * *